United States Patent [19]

Berg

[11] Patent Number: 5,338,410
[45] Date of Patent: Aug. 16, 1994

[54] SEPARATION OF 2-BUTANOL FROM T-AMYL ALCOHOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 181,792

[22] Filed: Jan. 18, 1994

[51] Int. Cl.$^5$ .................. B01D 3/36; C07C 29/84
[52] U.S. Cl. ............................ 203/57; 203/58; 203/60; 203/62; 203/63; 568/913
[58] Field of Search ............ 203/57, 58, 60, 62, 203/63, 51, 56; 568/913

[56] References Cited

U.S. PATENT DOCUMENTS 2,483,246 9/1949 Stribley .................. 203/70
4,756,803 7/1988 Berg ...................... 203/60

*Primary Examiner*—Wilbur Bascomb, Jr.

[57] ABSTRACT

2-Butanol is difficult to separate from t-amyl alcohol by conventional distillation or rectification because of the proximity of their boiling points. 2-Butanol can be readily separated from t-amyl alcohol by azeotropic distillation. Effective agents are ethyl acetoacetate, nitroethane and 3-pentanone.

1 Claim, No Drawings

SEPARATION OF 2-BUTANOL FROM T-AMYL ALCOHOL BY AZEOTROPIC DISTILLATION

FIELD OF THE INVENTION

This invention relates to a method for separating 2-butanol from t-amyl alcohol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

There are a number of commercial processes which produce complex mixtures of oxygenated organic compounds, e.g. the Fischer-Tropsch process. In this mixture, a series of homologous alcohols are often produced. Two of the commonest alcohols in this mixture are 2-butanol and t-amyl alcohol. 2-Butanol boils at 99.5° C. and t-amyl alcohol at 102.4° C. The relative volatility between these two is 1.13 which makes it very difficult to separate them by conventional rectification. Azeotropic distillation would be an attractive method of effecting the separation of 2-butanol from t-amyl alcohol if agents can be found that (1) will create a large apparent relative volatility between 2-butanol and t-amyl alcohol and (2) are easy to recover from 2-butanol. Table 1 shows the relative volatility required to obtain 99% purity. With no agent, the relative volatility is 1.18 and 100 actual plates are required. With an agent giving a relative volatility of 1.3, only 47 plates are required.

OBJECTIVE OF THE INVENTION

The object of this invention is to provide a process or method of azeotropic distillation that will enhance the relative volatility of 2-butanol from t-amyl alcohol in their separation in a rectification column. It is a further object of this invention to identify organic compounds which in addition to the above constraints, are stable, can be separated from 2-butanol and recycled to the azeotrope column with little decomposition.

TABLE 1

Theoretical and Actual Plates Required vs. Relative Volatility for 2-Butanol - t-Amyl Alcohol Separation

| Relative Volatility | Theoretical Plates Required At Total Reflux, 99% Purity | Actual Plates Required 75% Efficiency |
|---|---|---|
| 1.13 | 75 | 100 |
| 1.2 | 51 | 68 |
| 1.25 | 41 | 55 |
| 1.3 | 35 | 47 |

SUMMARY OF THE INVENTION

The objects of this invention are to provide a process for separating 2-butanol from t-amyl alcohol which entails the use of certain organic compounds as the agent in azeotropic distillation.

DETAILED DESCRIPTION OF THE INVENTION

TABLE 2

Effective Azeotropic Distillation Agents For Separating 2-Butanol From t-Amyl Alcohol

| Compounds | Relative Volatility |
|---|---|
| None | 1.13 |
| Acetonitrile | 1.2 |
| Tetrahydrofuran | 1.2 |
| Isopropyl acetate | 1.2 |
| n-Propyl acetate | 1.2 |
| Acetal | 1.25 |
| Ethyl isobutyrate | 1.2 |
| Ethyl acetoacetate | 1.25 |
| Methyl acetoacetate | 1.25 |
| Nitroethane | 1.2 |
| 2,2-Dimethoxypropane | 1.2 |
| 3-Pentanone | 1.3 |

I have discovered that certain organic compounds will greatly improve the relative volatility of 2-butanol to t-amyl and permit the separation of 2-butanol from t-amyl alcohol by rectification when employed as the agent in azeotropic distillation. Table 2 lists the compounds that I have found to be effective. They are acetonitrile, tetrahydrofuran, isopropyl acetate, n-propyl acetate, acetal, ethyl isobutyrate, ethyl acetoacetate, methyl acetoacetate, nitroethane, 2,2-dimeth oxypropane and 3-pentanone.

THE USEFULNESS OF THE INVENTION

The usefulness or utility of this invention can be demonstrated by referring to the data presented in Tables 1 and 2. All of the successful agents show that 2-butanol can be separated from t-amyl alcohol by means of azeotropic distillation in a rectification column and that the ease of separation as measured by relative volatility is considerable.

WORKING EXAMPLES

Example 1

Eighty grams of 2-butanol, 20 grams of t-amyl alcohol and 50 grams of ethyl acetoacetate were charged to a vapor-liquid equilibrium still and refluxed for four hours. Analysis indicated a vapor composition of 82.1% 2-butanol, 17.9% t-amyl alcohol; a liquid composition of 78.9% 2-butanol, 21.1% t-amyl alcohol. This is a relative volatility of 1.25.

Example 2

One hundred grams of a mixture comprising 80% t-amyl alcohol and 20% 2-butanol and 100 grams of 3-pentanone was placed in the stillpot of a 7.3 theoretical plate glass perforated plate rectification column and refluxed for two hours. The overhead composition was 58.8% 2-butanol, 41.2% t-amyl alcohol; the bottoms composition was 17.2% 2-butanol, 82.8% t-amyl alcohol which is a relative volatility of 1.3.

I claim:

1. A method for recovering 2-butanol from a mixture of 2-butanol and t-amyl alcohol which comprises distilling a mixture of 2-butanol and t-amyl alcohol in the presence of an azeotrope forming agent, recovering the 2-butanol and the azeotrope forming agent as overhead product and obtaining the t-amyl alcohol as bottoms product, wherein said azeotrope forming agent consists of one material selected from the group consisting of acetonitrile, tetrahydrofuran, isopropyl acetate, n-propyl acetate, acetal, ethyl isobutyrate, ethyl acetoacetate, methyl acetoacetate, nitroethane and 2,2-dimethoxypropane.

* * * * *